United States Patent [19]

Kobayashi et al.

[11] 4,324,929

[45] Apr. 13, 1982

[54] PROCESS FOR PRODUCING MONO, BIS OR TRIS(3,3,3-TRIFLUOROPROPYL)BENZENE

[75] Inventors: Yoshiro Kobayashi, Tokyo; Itsumaro Kumadaki, Hachiohji; Masaaki Takahashi, Tokyo; Takashi Yamauchi, Iwaki, all of Japan

[73] Assignee: Kureha Kagaku Kogyo Kabushiki Kaisha, Tokyo, Japan

[21] Appl. No.: 234,062

[22] Filed: Feb. 12, 1981

[30] Foreign Application Priority Data

Feb. 22, 1980 [JP] Japan .................................. 55-21094

[51] Int. Cl.³ ........................ C07C 17/28; C07C 25/14
[52] U.S. Cl. .................................... 570/127; 570/144
[58] Field of Search ................................ 570/127, 144

[56] References Cited

U.S. PATENT DOCUMENTS 2,862,974 12/1958 Sieglitz et al. .................. 570/144 X
3,080,428 3/1963 Weinmayr ...................... 570/144 X
3,253,046 5/1966 Teumac et al. ..................... 570/144

OTHER PUBLICATIONS

Yanichkin et al., CA 67:43486p, (1967).
Cleveland, CA 84:30620d, (1976).
Alal et al., CA 80:36820h, (1974).
Farkhadova et al., CA 79:52900u, (1973).
Schmerling, CA 44:2555c, (1950).
Weston, CA 48:10068a, (1954).
Yoneda et al., CA 72:21414q, (1970).
Mamedaliev et al., CA 62:3955g, (1965).

*Primary Examiner*—Thomas A. Waltz
*Attorney, Agent, or Firm*—Wegner & Bretschneider

[57] ABSTRACT

A process for producing mono, bis or tris(3,3,3-trifluoropropyl)benzene, which comprises bringing benzene into reaction with 3,3,3-trifluoropropylene in the presence of an acid catalyst selected from the group consisting of hydrogen fluoride, boron trifluoride and a mixture thereof, is disclosed.

5 Claims, No Drawings

PROCESS FOR PRODUCING MONO, BIS OR TRIS(3,3,3-TRIFLUOROPROPYL)BENZENE

BACKGROUND AND DETAILED DESCRIPTION OF THE INVENTION

The present invention relates to a process for producing mono, bis or tris(3,3,3-trifluoropropyl)benzene.

In prior arts, it is unknown reaction system that mono-, bis- or tris(3,3,3-trifluoropropyl)benzene is producing from 3,3,3-trifluoropropylene and benzene by Friedel-Crafts type reaction. As a process for producing 3,3,3-trifluoropropylbenzene, a certain process has been proposed in U.S. Pat. No. 3,080,428, in which process 3,3,3-trifluoropropyl ether is brought into reaction with benzene in the presence of hydrogen fluoride. However, since in the proposed process, water is formed from the reactants, the catalytic activity is reduced during the reaction and the recovery of once used catalyst is difficult. In addition, since the starting material, 3,3,3-trifluoropropyl ether, is obtained by the reaction of expensive vinylidene fluoride, formaldehyde or its polymer and hydrogen fluoride in a yield as low as 50 to 60%, the thus obtained 3,3,3-trifluoropropyl ether is highly expensive.

Whereas in the process of the present invention, since the product of the present invention is synthesized by the reaction of an industrial starting material, 3,3,3 -trifluoropropylene and benzene in the presence of an acid catalyst, not only the process needs only one reaction step but also the catalytic activity is maintained during and after the reaction is over because no water is formed by the above-mentioned reaction, and the recovery of the once used catalyst is extremely easy.

It is an object of the present invention to provide a process for producing 3,3,3-trifluoropropylated benzene derivative represented by the following formula

wherein n is an integer of 1, 2 or 3, which comprises bringing benzene into reaction with 3,3,3-trifluoropropylene in the presence of an acid catalyst selected from the group consisting of hydrogen fluoride, boron trifluoride and a mixture thereof. A further object is to provide bis(3,3,3-trifluoropropyl)benzene, and bis(3,3,3-trifluoropropyl)benzene obtained by the process thereabove. Other objects and advantages of the present invention will be apparent hereinafter.

Mono, bis or tris(3,3,3-trifluoropropyl)benzene is useful for a variety of purposes, for instance, in the organic synthesis of pharmaceuticals or agricultural chemicals as an intermediate compound.

Since 3,3,3-trifluoropropylene used in the process of the present invention has an electron-withdrawing group, trifluoromethyl, the basicity of the carbon-carbon double bond of the above-mentioned molecule of trifluoropropylene is far weaker than that of propylene having an electron-releasing group, methyl, a presence of a strongly acidic Friedel-Crafts' catalyst, is necessary in the reaction. However, in the case where aluminum chloride, i.e., a representative Friedel-Crafts' catalyst, is used, side reactions such as substitution by chlorine atom or cyclization of the reactants take place. For instance, in the reaction of benzene and 3,3,3-trifluoropropylene in the presence of aluminum chloride, the yield of 3,3,3-trifluoropropylbenzene is only a little with the by-production of (3-chloro-3,3-difluoropropyl)benzene; (3,3-dichloro-3-fluoropropyl)benzene; (3,3,3-trichloropropyl)benzene; 1,1-difluoroindan; 1-chloro-1-fluoroindan; 1,1-dichloroindan; etc.

On the other hand, ferric chloride which is weaker than aluminum chloride is almost ineffective in the present reaction. In addition, in the case where silica-alumina is used as the catalyst, the yield of the aimed compound is extremely poor due to the various side reactions.

As a result of keen efforts of the inventors of the present invention to find out a suitable catalyst for the purpose of the present reaction, hydrogen fluoride, boron trifluoride and a mixture thereof have been found to be the effective catalyst, and the present invention has been attained.

Since the catalyst used in the present process is a gaseous substance or a low-boiling liquid, the once used catalyst can be removed from the reaction system easily by stripping and the recovery and re-use of the once used catalyst are possibly carried out easily. In carrying out the process of the present invention, the catalyst is preferably used in an amount of more than 0.5 mole per mole of benzene.

The temperature of the reaction depends upon the species of catalyst. From the viewpoint of the catalytic activity, the temperature at which the catalyst shows its activity is highest in the case of hydrogen fluoride, followed by boron trifluoride and then by a mixture thereof. For instance, in the case of hydrogen fluoride, the reaction is preferably carried out at a temperature of 50° to 150° C.; in the case of boron trifluoride, the reaction is preferably carried out at a temperature of 0° to 120° C.; and, in that of a mixture of hydrogen fluoride and boron trifluoride, the reaction is preferably carried out at −20° to 100° C.

The reaction of the present process is shown by the following reaction formula:

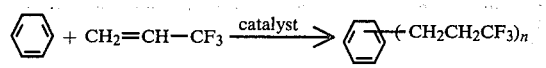

wherein n is an integer of 1, 2 or 3.

Namely, the reaction of the present process is quite different from the addition of propylene to aromatic compound, which gives isopropyl-substituted aromatic compound, and the presence of 3,3,3-trifluoropropyl group in the reaction product of the present process has been confirmed by the nuclear magnetic resonance spectra of $^1H$ and of $^{19}F$, respectively of the product of the present invention.

After the reaction of the present process is over, the residual gas is purged from the reaction system by stripping and the residue is neutralized, washed with water or filtered following the conventional steps, and the product is collected by distillation under a reduced pressure.

The preferable reaction condition for obtaining mainly mono- or bis(3,3,3-trifluoropropyl)benzene is shown in Table 1.

TABLE 1

Summary of preferable reaction condition

| Product | Reaction condition Molar amount of 3,3,3-trifluoropropylene per mole of benzene |
|---|---|
| Mono(3,3,3-trifluoropropyl)-benzene 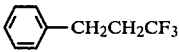 CH₂CH₂CF₃ | 0.5 ~ 1.5 |
| Bis(3,3,3-trifluoropropyl)-benzene 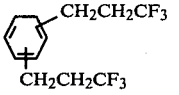 CH₂CH₂CF₃ / CH₂CH₂CF₃ | 1.5 ~ 2.5 |

The present invention is explained more precisely while referring to non-limitative examples as follows:

EXAMPLE 1

Into an autoclave made of stainless steel having a capacity of 1 l, 273 g of benzene, 72 g of anhydrous hydrogen fluoride and 364 g of 3,3,3-trifluoropropylene were introduced in the order, and while cooling the reaction tube with a mixture of dry-ice and methanol, boron trifluoride was pressured into the tube so that the internal pressure of the tube became 10 kg/cm².G. Then the tube was kept at a temperature of 20° C. to bring the content into reaction, the reaction having been carried out for 5 hours at 20° C. After the reaction was over, the residual gas was purged and the content of the tube was neutralized, washed with water and dried following the conventional steps. The results of ion-gas chromatography with FID while raising the temperature of the specimen of the thus obtained reaction product at a rate of 10° C./min are shown in Table 2 representing the weight ratio (in percentage) of the detected compounds.

Identification of each compound was carried by mass spectrometry and by $^1H$— and $^{19}F$— NMR, respectively.

TABLE 2

| Weight ratio (%) of the detected compounds | |
|---|---|
| Compounds | Weight ratio (%) |
| Benzene | 10.9 |
| (3,3,3-Trifluoropropyl)benzene | 59.5 |
| Bis(3,3,3-trifluoropropyl)benzene | 28.9 |
| Tris(3,3,3-trifluoropropyl)benzene | 0.7 |

By distilling the reaction mixture, i.e., the treated content of the reaction tube, (3,3,3-trifluoropropyl)benzene boiling at 155° to 157° C./760 mmHg and bis(3,3,3-trifluoropropyl)benzene boiling at 110° to 130° C./20 mmHg were obtained.

EXAMPLE 2

Into a reaction tube made of stainless steel having a capacity of 50 ml, 10 g of benzene, 1 g of anhydrous hydrogen fluoride and 7 g of 3,3,3-trifluoropropylene were introduced in the order, and while cooling the reaction tube with a mixture of dry-ice and methanol, boron trifluoride was pressured into the tube so that the internal pressure of the tube became 3 kg/cm².G. Then the tube was heated to 100° C. to bring the content into reaction, the reaction having been carried out for 40 hours at 100° C. After the reaction was over, the residual gas was purged and the content of the tube was neutralized, washed with water and dried following the conventional steps. The results of ion-gas chromatography with FID while raising the temperature of the specimen of the thus obtained reaction product at a rate of 10° C./min are shown in Table 3 representing the weight ratio (in percentage) of the detected compounds.

Identification of each compound was carried by mass spectrometry and by $^1H$— and $^{19}F$— NMR, respectively.

TABLE 3

| Weight ratio (%) of the detected compounds | |
|---|---|
| Compounds | Weight ratio (%) |
| Benzene | 30.0 |
| (3,3,3-Trifluoropropyl)benzene | 37.8 |
| Bis(3,3,3-trifluoropropyl)benzene | 23.2 |
| Tris(3,3,3-trifluoropropyl)benzene | 9.0 |

By distilling the reaction mixture, i.e., the treated content of the reaction tube, (3,3,3-trifluoropropyl)benzene boiling at 155° to 157° C./760 mmHg and bis(3,3,3-trifluoropropyl)benzene boiling at 110° to 130° C./20 mmHg were obtained.

EXAMPLE 3

In the same reaction tube used in Example 2, 10 g of benzene, 1 g of anhydrous hydrogen fluoride and 7 g of 3,3,3-trifluoropropylene were introduced in the order, and the tube was heated to 120° C. and kept at the same temperature for 48 hours to bring the content of the tube into reaction. After the reaction was over, the residual gas in the tube was purged, and the content of the tube was neutralized, washed with water and dried following the conventional steps. The results of the detection of the compounds in the content of the tube as in Example 1 are shown in Table 4.

TABLE 4

| Weight ratio (%) of the detected compounds | |
|---|---|
| Compound | Weight ratio (%) |
| Benzene | 71.3 |
| (3,3,3-trifluoropropyl)benzene | 26.4 |
| Bis(3,3,3-trifluoropropyl)benzene | 2.2 |
| Tris(3,3,3-trifluoropropyl)benzene | 0.1 |

EXAMPLE 4

Into an autoclave made of stainless steel having a capacity of 20 l, 2200 g of benzene, and 2710 g of 3,3,3-trifluoropropylene were introduced. The internal pressure of the tube was about 3 kg/cm².G. Then, boron trifluoride was pressured into the tube rapidly so that the internal pressure was raised to 50 kg/cm².G, and by immersing the tube into a warm water of 60° C., the content of the tube was brought into reaction.

The reaction was carried out for 20 hours, and after the reaction was over, the residual gas within the tube was purged. After collecting the content of the tube, the content was washed with water and dried following the conventional steps.

The results of the detection of the thus treated content with the same procedure as in Example 1 are shown in Table 5.

TABLE 5

| Weight ratio (%) of the detected compounds | |
|---|---|
| Compound | Weight ratio (%) |
| Benzene | 16.9 |

TABLE 5-continued

| Weight ratio (%) of the detected compounds | |
|---|---|
| Compound | Weight ratio (%) |
| (3,3,3-Trifluoropropyl)benzene | 58.1 |
| Bis(3,3,3-trifluoropropyl)benzene | 23.7 |
| Tris(3,3,3-trifluoropropyl)benzene | 1.3 |

EXAMPLE 5

Into the same reaction tube as in Example 2, 5 g of benzene, and 7 g of 3,3,3-trifluoropropylene were introduced. The internal pressure of the tube was about 3 kg/cm$^2$.G. Then, boron trifluoride was pressured into the tube rapidly so that the internal pressure was raised to 20 kg/cm$^2$.G, and by immersing the tube into a warm water of 60° C., the content of the tube was brought into reaction.

The reaction was carried out for 15 hours, and after the reaction was over, the residual gas within the tube was purged. After collecting the content of the tube, the content was washed with water and dried following the conventional steps.

The results of the detection of the thus treated content with the same procedure as in Example 1 are shown in Table 6.

TABLE 6

| Weight ratio (%) of the detected compounds | |
|---|---|
| Compound | Weight ratio (%) |
| Benzene | 62.8 |
| (3,3,3-Trifluoropropyl)benzene | 32.8 |
| Bis(3,3,3-trifluoropropyl)benzene | 4.1 |
| Tris(3,3,3-trifluoropropyl)benzene | 0.30 |

Comparative Example 1

Into 5 ml of benzene, 0.3 g of anhydrous aluminum trichloride was dispersed, and 3,3,3-trifluoropropylene was bubbled into the thus formed dispersion at an ordinary temperature under an ordinary pressure. In this occasion, the colour of aluminum chloride changed from yellow to reddish brown with the visible formation of so-called red oil. The gas-bubbling was carried out for one hour and then the reaction mixture was poured into 20 ml of water. The organic layer was washed with water and dried following the conventional steps. The results of the examination by ion-gas chromatography as in Example 1 and further by mass-spectrography and by nuclear magnetic resonance spectroscopy of the reaction product are shown in Table 7.

TABLE 7

| Weight ratio (%) of the detected compounds | |
|---|---|
| Compound | Weight ratio (%) |
| Benzene | 87.9 |

TABLE 7-continued

| Weight ratio (%) of the detected compounds | |
|---|---|
| Compound | Weight ratio (%) |
| 1,1-Difluoroindan | 7.6 |
| 1-Chloro-1-fluoroindan | 0.9 |
| 1,1-Dichloroindan | less than 0.1 |
| (3,3,3-Trifluoropropyl)benzene | less than 0.1 |
| (3-Chloro-3,3-difluoropropyl)benzene | less than 0.1 |
| (3,3-Dichloro-3-fluoropropyl)benzene | less than 1.0 |
| (3,3,3-Trichloropropyl)benzene | less than 0.1 |

Comparative Example 2

Into a 200-ml autoclave made of stainless steel, 100 ml of benzene and 10 g of a silica-alumina catalyst (Type: N-633L, manufactured by Nikki Kagaku Co., Japan) were introduced and 20 g of 3,3,3-trifluoropropylene was further introduced into the autoclave. Upon heating the autoclave to bring the internal temperature to 220° C., the internal pressure showed 22 kg/cm$^2$.G. During the period of one hour when the temperature was maintained at 220° C., the internal pressure did not show any change. After that, the autoclave was cooled to room temperature, and the residual gas was purged. After subjecting the content of the autoclave to gas chromatography, the formation of 3,3,3-trifluoropropylbenzene was scarcely detected because of the appearance of the extremely minute peak corresponding to the compound.

What is claimed is:

1. A process for producing a 3,3,3-trifluoropropylated benzene derivative represented by the following formula

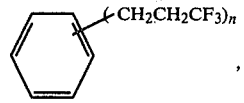

wherein n is an integer of 1, 2 or 3, which comprises bringing benzene into reaction with 3,3,3-trifluoropropylene in the presence of an acid catalyst selected from the group consisting of hydrogen fluoride, boron trifluoride and a mixture thereof.

2. The process according to claim 1, wherein benzene is brought into reaction with 3,3,3-trifluoropropylene in the presence of hydrogen fluoride at a temperature of from 50° to 150° C.

3. The process according to claim 1, wherein benzene is brought into reaction with 3,3,3-trifluoropropylene in the presence of boron trifluoride at a temperature of from 0° to 120° C.

4. The process according to claim 1, wherein benzene is brought into reaction with 3,3,3-trifluoropropylene in the presence of the mixture of hydrogen fluoride and boron trifluoride at a temperature of from −20° to 100° C.

5. Bis(3,3,3-trifluoropropyl)benzene.

* * * * *